US009209468B2

(12) United States Patent
Chen et al.

(10) Patent No.: US 9,209,468 B2
(45) Date of Patent: Dec. 8, 2015

(54) FUEL CELL FAILURE PREDICTION APPARATUS

(71) Applicant: Industrial Technology Research Institute, Hsinchu (TW)

(72) Inventors: Chi-Chang Chen, Changhua County (TW); Dein Shaw, Hsinchu (TW); Shiauh-Ping Jung, Taoyuan County (TW); Chun-I Lee, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 205 days.

(21) Appl. No.: 13/868,110

(22) Filed: Apr. 23, 2013

(65) Prior Publication Data

US 2014/0162160 A1  Jun. 12, 2014

(30) Foreign Application Priority Data

Dec. 7, 2012  (TW) .............................. 101146109 A (51) Int. Cl.
*H01M 8/04* (2006.01)
*G01N 27/416* (2006.01)

(52) U.S. Cl.
CPC ......... *H01M 8/04679* (2013.01); *G01N 27/416* (2013.01); *G01N 27/4161* (2013.01); *H01M 8/0494* (2013.01); *H01M 8/04552* (2013.01); *H01M 8/04664* (2013.01); *H01M 8/04671* (2013.01); *H01M 8/04701* (2013.01); *H01M 8/04731* (2013.01); *H01M 8/04791* (2013.01); *H01M 8/04798* (2013.01);

(Continued)

(58) Field of Classification Search
CPC ..................... H01M 8/04664; H01M 8/04671; H01M 8/04679; H01M 8/04828; H01M 8/04701; H01M 8/04791; H01M 8/04798; G01N 27/4161; G01N 27/416
See application file for complete search history.

(56) References Cited

U.S. PATENT DOCUMENTS

| 6,103,409 A | 8/2000 | DiPierno Bosco et al. |
| 6,461,751 B1 | 10/2002 | Boehm et al. |
| 6,815,107 B2 | 11/2004 | Inai et al. |

(Continued)

FOREIGN PATENT DOCUMENTS

| CN | 101188298 | 5/2008 |
| CN | 101542810 | 9/2009 |

(Continued)

OTHER PUBLICATIONS

Machine Translation of JP 2007-317553 A.*

(Continued)

*Primary Examiner* — Jonathan Jelsma
(74) *Attorney, Agent, or Firm* — Jianq Chyun IP Office (57) ABSTRACT

A fuel cell failure prediction apparatus is provided. The prediction apparatus includes upstream and downstream voltage monitoring units, a data processing unit and a system control unit. The upstream and downstream voltages of each single cell may be synchronously monitored by the upstream and downstream voltage monitoring units. According to the monitored upstream and downstream voltages of each single cell, the data processing unit is used to obtain a differential voltage of the upstream and downstream voltages of each single cell. In accordance with the differential voltage, the system control unit performs a correcting control of failure prediction on the fuel cell.

16 Claims, 10 Drawing Sheets (52) U.S. Cl.
CPC .......... *H01M 8/04828* (2013.01); *Y02E 60/50* (2013.01); *Y02E 60/521* (2013.01)

(56) References Cited

U.S. PATENT DOCUMENTS

| | | | |
|---|---|---|---|
| 7,704,619 | B2 | 4/2010 | Fujii et al. |
| 7,781,118 | B2 | 8/2010 | Trabold et al. |
| 7,887,962 | B2 | 2/2011 | Nakanishi |
| 8,268,497 | B2 | 9/2012 | Takada et al. |
| 2003/0022044 | A1 | 1/2003 | Inai et al. |
| 2006/0183005 | A1* | 8/2006 | Yip et al. ............... 429/12 |
| 2006/0188766 | A1 | 8/2006 | Fujii et al. |
| 2008/0311452 | A1 | 12/2008 | Takada et al. |
| 2012/0196201 | A1 | 8/2012 | Bernard |

FOREIGN PATENT DOCUMENTS

| | | |
|---|---|---|
| JP | 2007172962 | 7/2007 |
| JP | 2007-317553 | 12/2007 |
| JP | 2008-262824 | 10/2008 |
| JP | 2009037762 | 2/2009 |
| JP | 2009-70576 | 4/2009 |
| JP | 2009259758 | 11/2009 |
| JP | 2011238360 | 11/2011 |
| JP | 2012004101 | 1/2012 |
| TW | 200500621 | 1/2005 |
| TW | M424627 | 3/2012 |
| WO | 2011021301 | 2/2011 |

OTHER PUBLICATIONS

Wu et al, "Diagnostic tools in PEM fuel cell research: Part I Electrochemical techniques," International Journal of Hydrogen Energy 33, Mar. 2008, pp. 1735-1746.

Wu et al., "Diagnostic tools in PEM fuel cell research: Part II Physical/chemical methods," International Journal of Hydrogen Energy 33, Mar. 2008, pp. 1747-1757.

Niroumand et al., "PEM fuel cell low flow FDI," Journal of Process Control 21, Apr. 2011, pp. 602-612.

Li et al., "A review of water flooding issues in the proton exchange membrane fuel cell," Journal of Power Sources 178, Mar. 15, 2008, pp. 103-117.

Barbir et al., "Relationship between pressure drop and cell resistance as a diagnostic tool for PEM fuel cells," Journal of Power Sources 141, Feb. 16, 2005, pp. 96-101.

Schmittinger et al., "A review of the main parameters influencing long-term performance and durability of PEM fuel cells," Journal of Power Sources 180, May 15, 2008, pp. 1-14.

"Office Action of Japan Counterpart Application", issued on May 20, 2014, p. 1-p. 4, in which the listed references were cited.

"Office Action of Taiwan Counterpart Application", issued on Apr. 25, 2014, p. 1-p. 7, in which the listed references were cited.

"Notice of allowance of Japan Counterpart Application", issued on Aug. 25, 2015, p. 1-p. 3, in which the listed references were cited.

* cited by examiner

FUEL CELL FAILURE PREDICTION APPARATUS

CROSS-REFERENCE TO RELATED APPLICATION

This application claims the priority benefit of Taiwan application serial no. 101146109, filed on Dec. 7, 2012. The entirety of the above-mentioned patent application is hereby incorporated by reference herein and made a part of this specification.

TECHNICAL FIELD

The disclosure relates to a prediction apparatus and a prediction method for performance degradation and failure of a fuel cell.

BACKGROUND

Along with progress of industry, consumption of traditional energy sources such as coal, oil and nature gas continually rises, and since stock of the nature energy sources is limited, a new alternative energy source has to be developed to replace the traditional energy sources, and a fuel cell is an important an practical selection.

In brief, the fuel cell is basically a power generation device capable of converting chemical energy into electrical energy through a reverse reaction of water electrolysis. Regarding a proton exchange membrane fuel cell, it is mainly composed of a membrane electrode assembly (MEA) and two electrode plates.

The MEA has an anode and a cathode, and a fuel (for example, hydrogen) is transmitted through the anode, and an oxidant (for example, air) with humidity is transmitted through the cathode, where an oxidation reaction is taken place at the anode, and a reduction reaction is taken place at the cathode, and a chemical formula thereof is as follows:

Anode: $H_2 \rightarrow 2H^+ + 2\ e^-$
Cathode: $O_2 + 4H^+ + 4\ e^- \rightarrow 2H_2O$ When the hydrogen of the anode contacts a catalyst adjacent to the proton exchange membrane, hydrogen molecules are dissociated into hydrogen ions and electrons, where the electrons flow in an electrical circuit, and the hydrogen ions directly pass through the proton exchange membrane from the anode to reach the cathode. Under a function of a cathode catalyst, the electrons reached through the electrical circuit are combined with oxygen to form oxygen ions, and the oxygen ions are combined with the hydrogen ions passing through the proton exchange membrane to form water molecules, which is the oxidation and reduction reaction process of electrochemical, and electricity is provided to a load through the electrical circuit.

However, the cost and lifespan of the fuel cell are major obstacles for commercialization of the fuel cell, and system problems caused by water and heat management and stoichiometry control has to be first resolved.

SUMMARY

One of exemplary embodiments comprises a prediction apparatus for failure of a fuel cell. The fuel cell includes at least one single cell. The prediction apparatus includes upstream and downstream voltage monitoring units, a data processing unit and a system control unit. The upstream and downstream voltage monitoring units correspond to each of the single cells and synchronously monitor an upstream voltage and a downstream voltage of each single cell. The data processing unit receives voltage signals of the upstream voltage and the downstream voltage to obtain a differential voltage (DV) of the upstream voltage and the downstream voltage of each single cell. The system control unit performs a correction control of failure prediction on the fuel cell according to the differential voltage.

Another of exemplary embodiments comprises a prediction method for failure of a fuel cell. The fuel cell includes at least one single cell. The prediction method includes measuring an upstream voltage and a downstream voltage of each single cell to obtain a differential voltage (DV) of the upstream voltage and the downstream voltage, and determining whether the differential voltage is within a tolerance interval, and performing correction when the differential voltage exceeds the tolerance interval.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
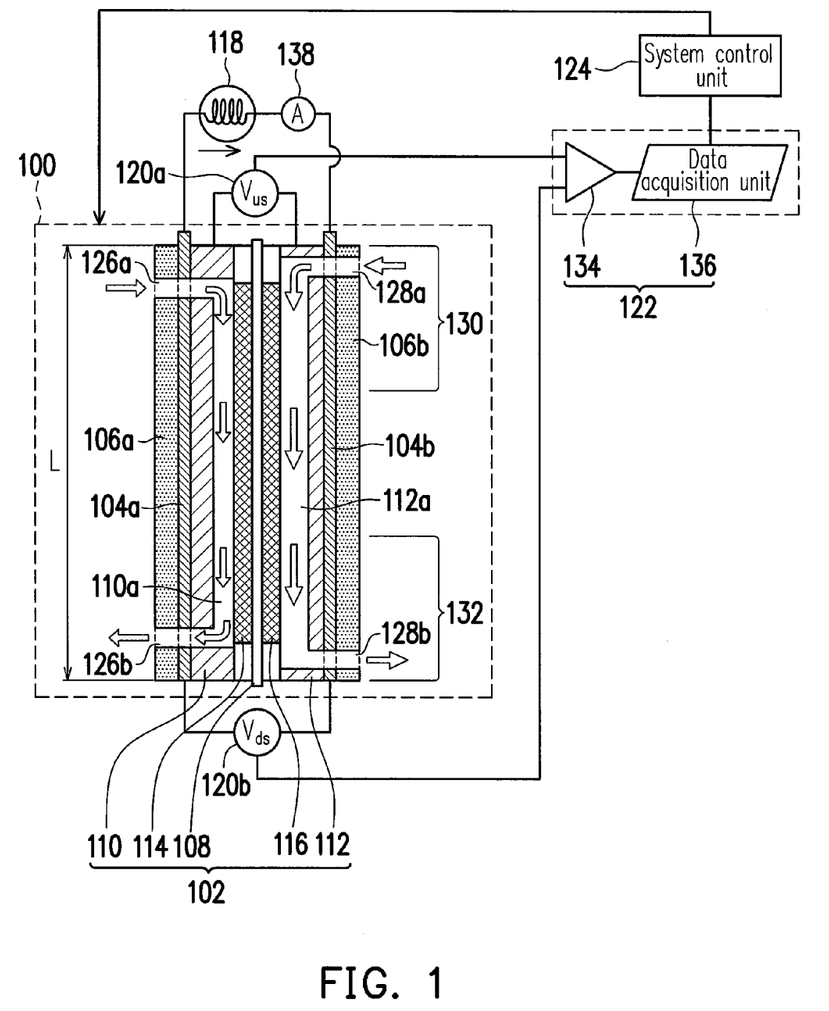
FIG. 1 is a schematic diagram of a prediction apparatus for failure of a fuel cell according to a first embodiment of the disclosure.

FIG. 1 is a schematic diagram of a prediction apparatus for failure of a fuel cell according to a first embodiment of the disclosure.

Referring to FIG. 1, the fuel cell 100 in the first embodiment includes a single cell 102. Moreover, the fuel cell 100 may include a pair of current collectors 104a and 104b located at two sides of the single cell 102, and a pair of end plates 106a and 106b respectively located next to the pair of current collectors 104a and 104b, for example. The single cell 102 may include a membrane electrode assembly (MEA) 108, an anode flow field plate 110, a cathode flow field plate 112, an anode gas diffusion layer (GDL) 114 and a cathode gas diffusion layer 116, though the disclosure is not limited thereto. The anode flow field plate 110, for example, includes an anode flow channel 110a used for transporting a fuel (hydrogen), and the cathode flow field plate 112 includes a cathode flow channel 112a used for transporting oxidant (air). When operating the fuel cell 112, the hydrogen molecules of the anode is dissociated into hydrogen ions and electrons, where the electrons flow through the anode flow field plate 110, the current collector 104a and a load 118, and enter the current collector 104b and the cathode flow field plate 112, and the hydrogen ions directly pass through the MEA 108 from the anode to reach the cathode. The electrons reaching the cathode are combined with oxygen to form oxygen ions, and the oxygen ions are combined with the hydrogen ions passing through the MEA 108 to form water molecules.

In FIG. 1, the prediction apparatus includes upstream and downstream voltage monitoring units 120a and 120b, a data processing unit 122 and a system control unit 124. In one embodiment, the anode flow field plate 110 and the cathode flow field plate 112 are defined to have three equal parts of a total length L, where an L/3 length region near a fuel inlet manifold 126a and an oxidant inlet manifold 128a are referred to as an upstream 130, and an L/3 length region near a fuel outlet manifold 126b and an oxidant outlet manifold 128b are referred to as a downstream 132. In another embodiment, an L/2~L/4 length region near the fuel inlet manifold 126a and the oxidant inlet manifold 128a are referred to as the upstream 130, and an L/2~L/4 length region near the fuel outlet manifold 126b and the oxidant outlet manifold 128b are referred to as the downstream 132. The upstream voltage monitoring unit 120a of the first embodiment is an upstream voltmeter, and the downstream voltage monitoring unit 120b is a downstream voltmeter. A position of voltages monitored by the upstream voltmeter 120a is any position in the region of the upstream 130, and a position of voltages monitored by the downstream voltmeter 120b is any position in the region of the downstream 132, where positions adjacent to the oxidant inlet manifold 128a and the oxidant outlet manifold 128b are preferred monitoring positions.

The data processing unit 122 of the first embodiment may have a data operation unit and a data acquisition unit 136. After receiving voltage signals of an upstream voltage $V_{us}$ measured by the upstream voltmeter 120a and a downstream voltage $V_{ds}$ measured by the downstream voltmeter 120b, an operational amplifier 134, a subtractor, or software may be used as the data operation unit to calculate a differential voltage $DV_{cell}$ between the upstream voltage $V_{us}$ and the downstream voltage $V_{ds}$ of the single cell 102 and transmit the differential voltage $DV_{cell}$ to the data acquisition unit 136. Then, the system control unit 124 performs a correction control of failure prediction on the fuel cell 100 according to the differential voltage $DV_{cell}$.

The correction control of failure prediction of the system control unit 124 is described below.

When the external load 118 starts to operate, and a load current is gradually increased from zero, a current meter 138 measures the current, and the upstream voltmeter 120a and the downstream voltmeter 120b of the prediction apparatus of the first embodiment are used to gradually monitor. In this way, a curve diagram of the differential voltage $DV_{cell}$ of the fuel cell 100 and the current (DV-I) is obtained as that shown in FIG. 2.

Figure 2:
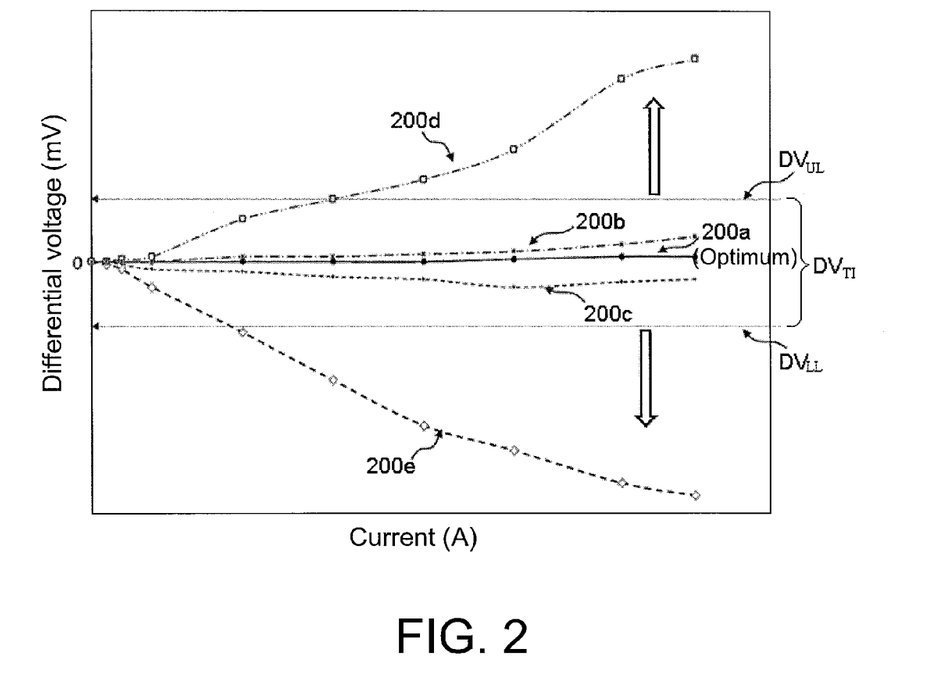
FIG. 2 is a curve diagram of differential voltage ($DV_{cell}$)  and current (DV-I) of a fuel cell of the first embodiment.

FIG. 2 displays curves of 5 parameters, which are respectively parameters 200a, 200b, 200c, 200d and 200e. According to FIG. 2, it is known that the operating parameter 200a is the best condition, and the differential voltage thereof is close to 0 mV ($DV_{cell}$~0 mV) at any load current, which represents that water control (i.e. relative humidity of the fuel and the oxidation) and stoichiometry control are all the best condition If the result of the parameter 200a is taken as a reference base, when the differential voltage is positive ($DV_{cell}>0$) parameters 200b and 200d, it represents that the upstream voltage is greater than the downstream voltage ($V_{us}>V_{ds}$), and the further a developing trend thereof deviates from the differential voltage of 0 ($DV_{cell}=0$), the poorer the stoichiometry control is, which also represents that the stoichiometry of the fuel cell is in a lack in state. When the differential voltage is negative ($DV_{cell}<0$) parameters 200c and 200e, it represents that the upstream voltage is smaller than the downstream voltage ($V_{us}<V_{ds}$), and the further the developing trend thereof deviates from the differential voltage of 0 ($DV_{cell}=0$), the poorer the water control is, which also represents that the fuel cell is in a dry out state.

However, the fuel cell is a very complicated electrochemical reaction field, and a plurality of parameters can influence performance of the fuel cell, in which besides the water control and the stoichiometry control, factors of structure stress, temperature and pressure, etc. can also influence the performance of the fuel cell. Therefore, a tolerance interval $DV_{TI}$ is set to improve reliability of the prediction, where the tolerance interval $DV_{TI}$ includes an upper limit $DV_{UL}$ and a lower limit $DV_{LL}$.

According to the upper limit $DV_{UL}$ and the lower limit $DV_{LL}$ of the tolerance interval $DV_{TI}$, the parameters 200b and 200c of FIG. 2 still belong to tolerable operating parameters. The parameter 200d is a tolerable stoichiometry in a low current load, and in case of a high current load, the stoichiometry of the fuel cell is changed from the lack in state to a starvation state. The parameter 200e is also a tolerable water control state in case of the low current load, and in case of the high current load, the fuel cell is changed from a dry out state to a dehydration state. Therefore, the parameters 200d and 200e may all cause failure, and all require a corresponding correction of improper water control and a corresponding correction of improper stoichiometry control. The correction of the improper water control is, for example, at least one of the measures of increasing relative humidity, reducing a temperature of the fuel cell and reducing the stoichiometry. The correction of the improper stoichiometry control is, for example, at least one of the measures of increasing the stoichiometry, reducing an output power of the fuel cell, increasing the temperature of the fuel cell and reducing the relative humidity. A plurality of the above measures can be simultaneously implemented, or only one of the above measures is implemented.

If a load constant current mode is used, there are 7 stoichiometry parameters, which are respectively S0, S1, S2, S3, S4, S5 and S6, in which S0 is the optimal. Taking S0 as a reference, the more to the right the lower the stoichiometry is, and the more to the left the higher the stoichiometry is. By using the prediction apparatus of the first embodiment to monitor, a monitoring result is as that shown in FIG. 3A and FIG. 3B.

Figure 3A:
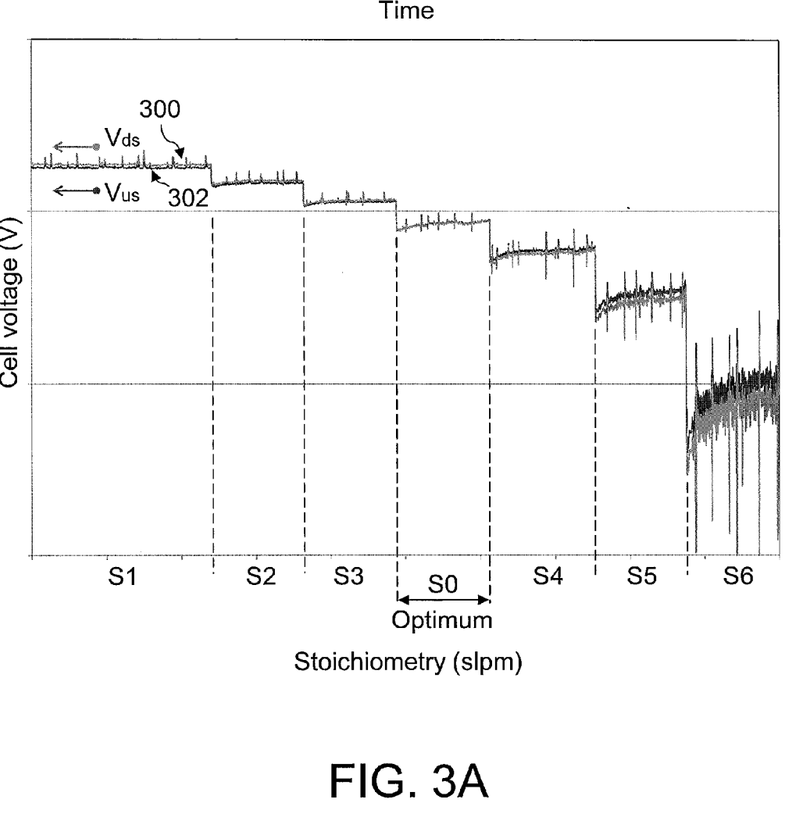
FIG. 3A is a curve diagram of an upstream voltage $V_{us}$ and a downstream voltage $V_{ds}$ of the fuel cell of the first embodi-  ment varied along with time under different stoichiometry.
Figure 3B:
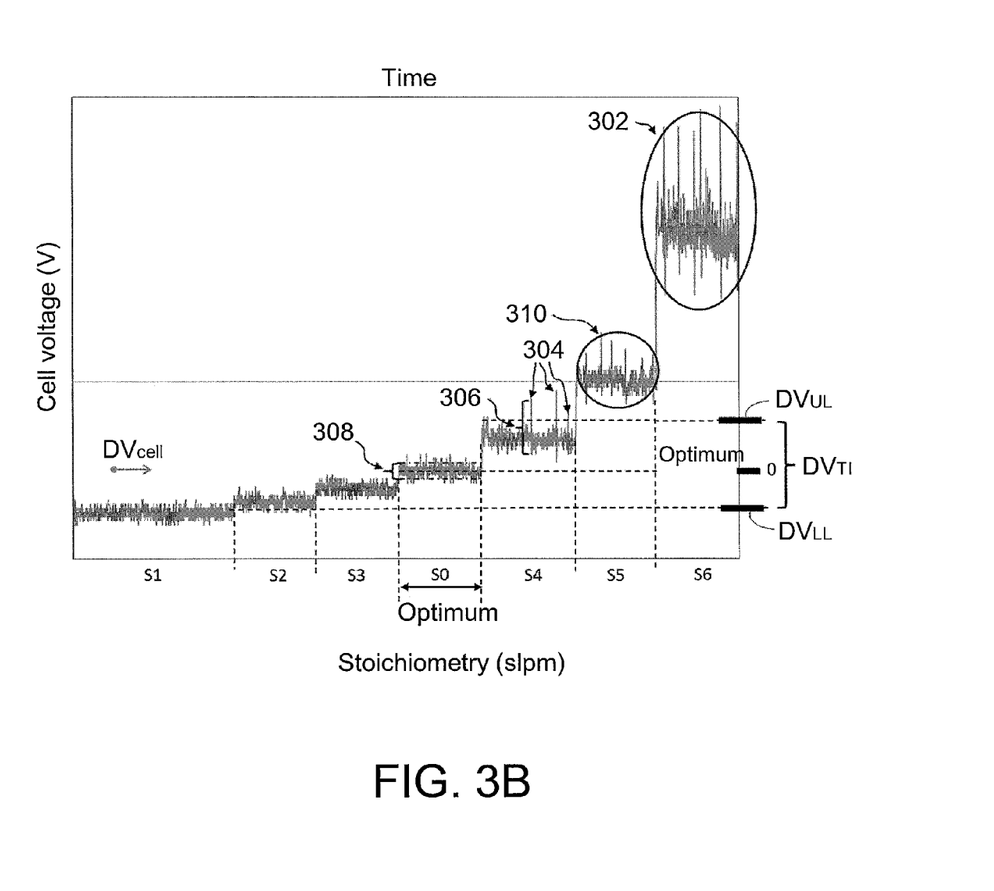
FIG. 3B is a curve diagram of the differential voltage $DV_{cell}$ of FIG. 3A varied along with time.

FIG. 3A is a curve diagram of the upstream voltage $V_{us}$ and the downstream voltage $V_{ds}$ varied along with time under different stoichiometry. FIG. 3B is a curve diagram of the differential voltage $DV_{cell}$ of FIG. 3A varied along with time.

A monitoring result of the upstream voltage $V_{us}$ monitored by the upstream voltmeter 120a of FIG. 1 is shown as a curve 302 of FIG. 3A, and a monitoring result of the downstream voltage $V_{ds}$ monitored by the downstream voltmeter 120b of FIG. 1 is shown as a curve 300 of FIG. 3A. When the curves 300 and 302 of FIG. 3A are converted into the differential voltage $DV_{cell}$ by the operational amplifier 134 of FIG. 1, a result thereof is shown in FIG. 3B.

According to the result of the differential voltage $DV_{cell}$, it is known that under a state of the stoichiometry S0, the differential voltages thereof are all close to 0 mV ($DV_{cell} \approx 0$ mV), which is the best stoichiometry control condition, and the suitable tolerance interval $DV_{TI}$ is set, where the tolerance interval $DV_{TI}$ includes the upper limit $DV_{UL}$, and the lower limit $DV_{LL}$. When the differential voltage is positive ($DV_{cell}1>0$), it represents that the fuel cell is in an under-stoichiometry state, and when the differential voltage is greater than the upper limit ($DV_{cell}>DV_{UL}$), it represents that the fuel cell enters the lack in state or even the starvation state, for example, the stoichiometry S5 and the stoichiometry S6. Comparatively, when the differential voltage is negative ($DV_{cell}<0$), it represents that the fuel cell is in an over-stoichiometry state, and when the differential voltage is smaller than the lower limit ($DV_{cell}<DV_{UL}$), it represents that parasitic power loss of balance of plant (BOP) of the system is excessive, the system efficiency is decreased, and the fuel cell is gradually dried, for example, the stoichiometry S1. Therefore, the aforementioned correction of the improper stoichiometry control is required to be performed.

Moreover, in the embodiment, besides the fuel cell stoichiometry control and a developing trend are predicted, liquid water overflow can also be detected. When it is monitored that the differential voltage has a momentary peak 304 during the operation of the fuel cell 100 of FIG. 1, it represents that the liquid water overflow is appeared in the fuel cell. An amplitude 306 of the peak 304 is defined to be twice of an average amplitude 308 of the differential voltage, though the disclosure is not limited thereto. A defined value of the "peak" can be different as the flow channel and configuration type of the flow field plate are different.

When the peak starts to frequently occur, it represents that the fuel cell 100 of FIG. 1 is in a severe stoichiometry lack in state, for example, the curve 310 of the stoichiometry S5. Here, a peak occurrence frequency of more than 0.01 Hz is defined as "frequent", though since the flow channel and configuration type of the flow field plate are different, the defined value is also different. If the peak enters a high-frequency oscillation, it represents that the fuel cell of FIG. 1 is in the starvation state, and the liquid water overflows, for example, the curve 312 of the stoichiometry S6. The above situations may all cause failure of the fuel cell. Therefore, the corresponding correction of the water overflow is required, for example, the fuel and the oxidant is supplied to the fuel cell 100 to drain the water. Here, the peak occurrence frequency of more than 0.05 Hz is defined as "high frequency", though a defined value of the "peak" can be different as the flow channel and configuration type of the flow field plate are different.

Figure 4:
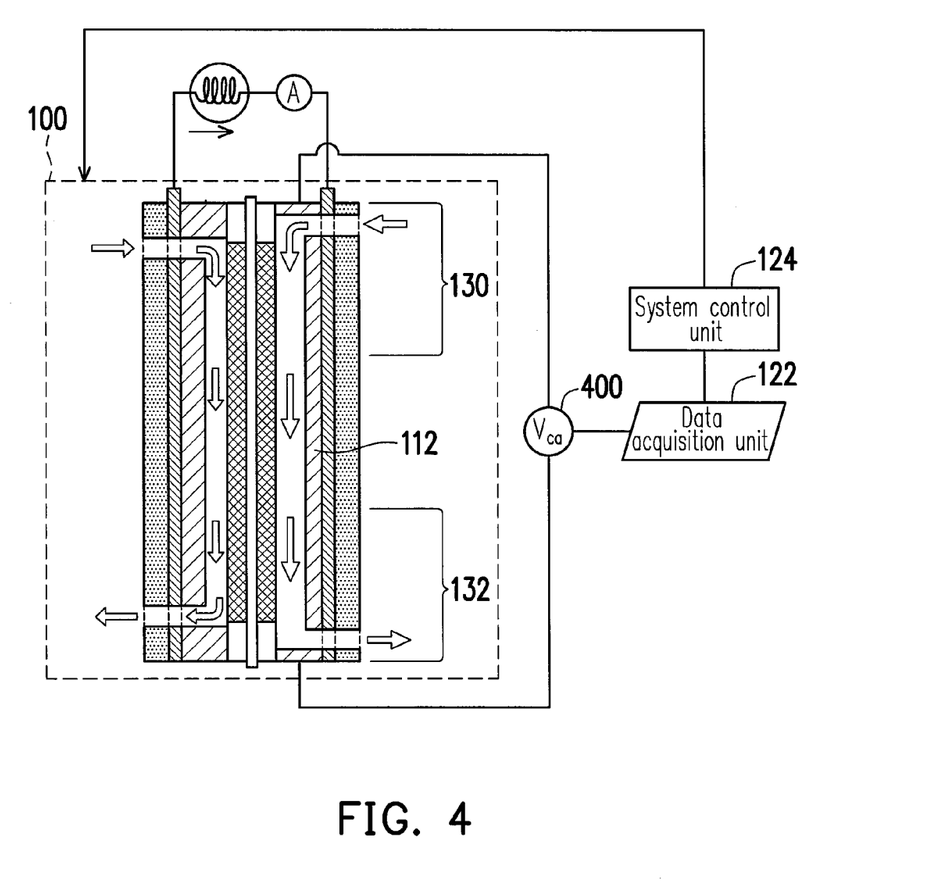
FIG. 4 is a variation of the prediction apparatus for failure of a fuel cell of FIG. 1.
Figure 5:
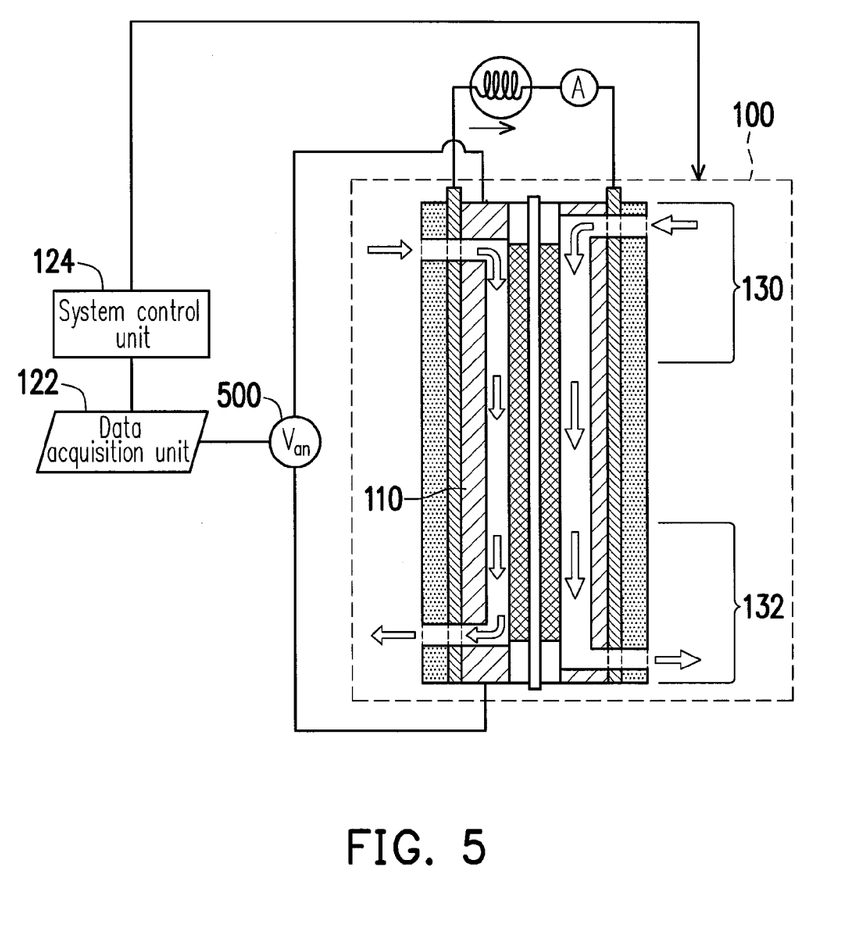
FIG. 5 is another variation of the prediction apparatus for failure of a fuel cell of FIG. 1.

Besides FIG. 1, the prediction apparatus for failure of the fuel cell may further has two variations as that shown in FIG. 4 and FIG. 5.

FIG. 4 is a variation of the prediction apparatus for failure of a fuel cell of FIG. 1. FIG. 5 is another variation of the prediction apparatus for failure of a fuel cell of FIG. 1. In FIG. 4 and FIG. 5, device symbols the same to that in FIG. 1 are used to denote the same or similar components, where a cathode voltmeter 400 is used in FIG. 4 to serve as the upstream and downstream voltage monitoring units to measure a voltage value ($V_{ca}$) between the upstream and the downstream of the cathode flow field plate 112. In FIG. 5, an anode voltmeter 500 is used to serve as the upstream and downstream voltage monitoring units to measure a voltage value ($V_{an}$) between the upstream and the downstream of the anode flow field plate 110.

Figure 6:
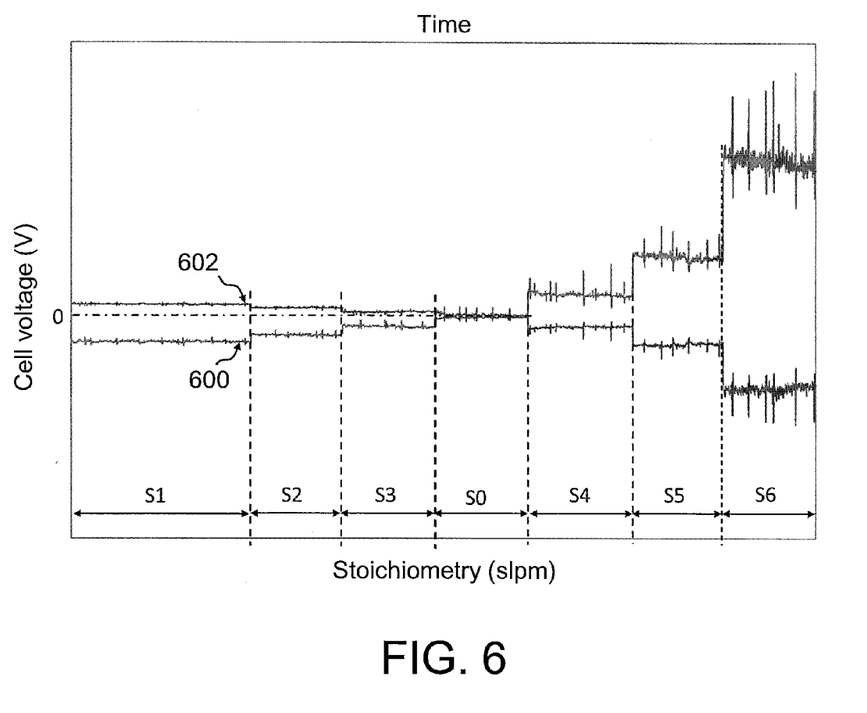
FIG. 6 is a curve diagram of differential voltages of FIG. 4 and FIG. 5 varied along with time under different stoichiometry.

The same to the embodiment of FIG. 3B, the load constant current mode and 7 stoichiometry parameters S0-S6 are used to obtain a monitoring result as that shown in FIG. 6, in which a cathode differential voltage curve ($V_{ca}$) 600 is a result monitored through the cathode voltmeter 400, and a prediction trend thereof is that the differential voltage is gradually increased as the stoichiometry is gradually reduced, which is the same to the trend of FIG. 3B.

An anode differential voltage curve ($V_{ca}$) 602 in FIG. 6 is a result monitored through the anode voltmeter 500, and a prediction trend thereof is that the differential voltage is gradually reduced as the stoichiometry is gradually reduced, which is opposite to the trend of FIG. 3B. Therefore, if the prediction apparatus of FIG. 5 is used and the correction controls of FIG. 2 and FIG. 3 are applied, a logic of [($V_{an} \times (-1)$)] is used to obtain a same prediction mode to determine a cell state.

Figure 7:
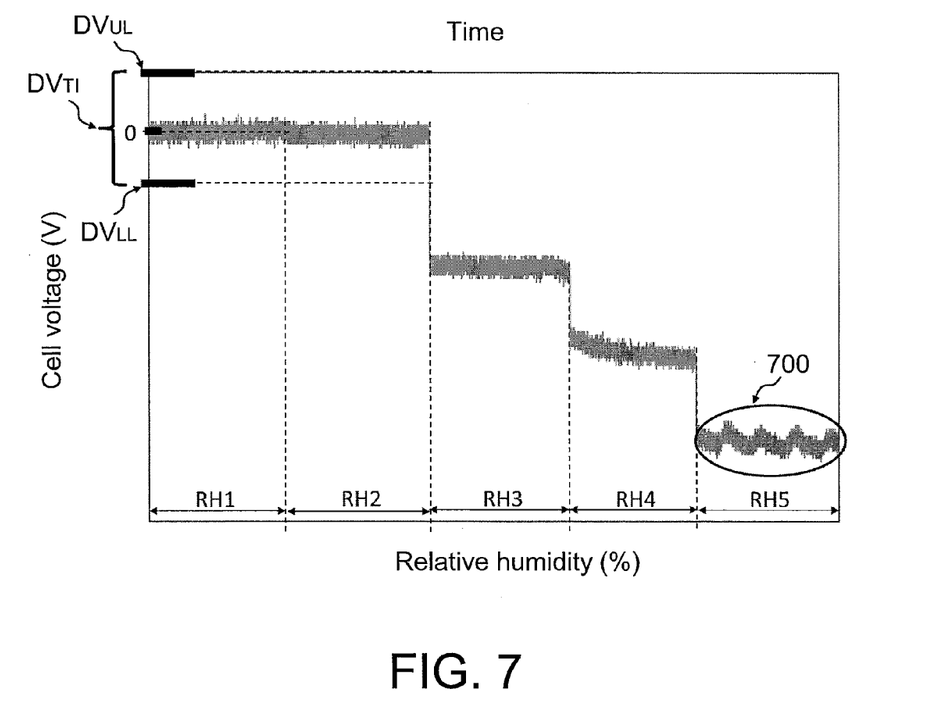
FIG. 7 is a curve diagram of a differential voltage of the fuel cell of the first embodiment varied along with time under different humidity.

Moreover, If a load constant current and constant stoichiometry mode is used, there are 5 water control parameters, which are respectively RH1, RH2, RH3, RH4 and RH5. By using the prediction apparatus to monitor, a monitoring result is as that shown in FIG. 7. According to the result of the differential voltage ($DV_{cell}$), it is known that under a state of the relative humidity RH1, the differential voltages thereof are all close to 0 mV ($DV_{cell} \approx 0$ mV), which is the best relative humidity condition, and a suitable differential voltage tolerance interval $DV_{TI}$ is set, which includes an upper limit $DV_{UL}$ and a lower limit $DV_{LL}$, where determination criterions of the three parameters of the tolerance interval $DV_{TI}$, the upper limit $DV_{UL}$ and the lower limit $DV_{LL}$ are the same in the same fuel cell 100 (values the same to that of the first embodiment can be used). When the differential voltage is negative ($DV_{cell}<0$), and is smaller than the lower limit ($DV_{cell}<DV_{LL}$), it represents that the fuel cell is in the dry out state, for example, the relative humidity RH3, RH4 and RH5. Moreover, in the present embodiment, besides the fuel cell water control and a developing trend are predicted, a dehydration phenomenon of the fuel cell can also be detected. Namely, during the operation process of the fuel cell 100, if it is detected that the differential voltage has a periodic fluctuation 700, it represents that the fuel cell 100 has a severe dehydration phenomenon, which may cause failure of the fuel cell 100, so that a corresponding precaution measure is required.

Figure 8:
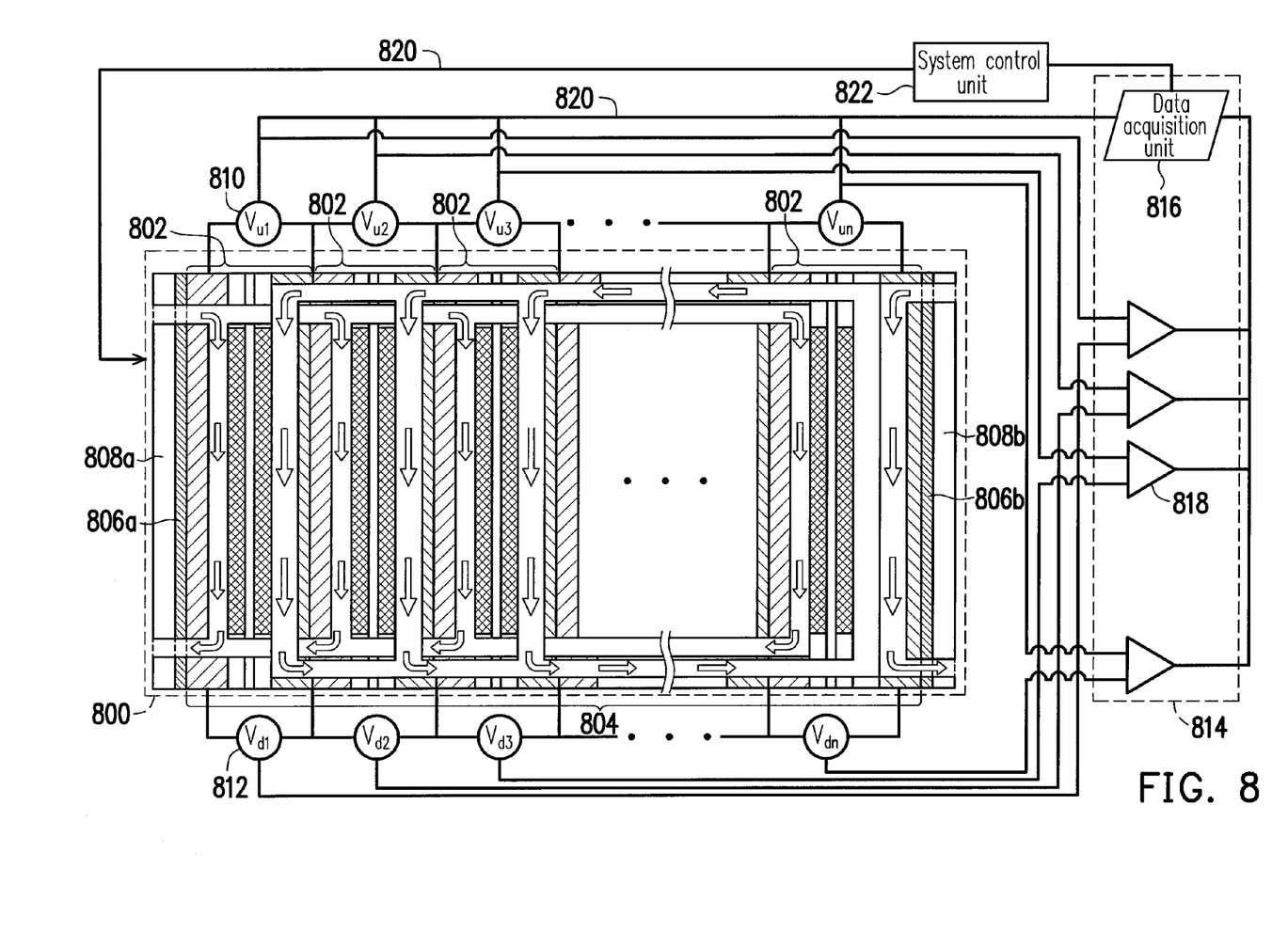
FIG. 8 is a schematic diagram of a prediction apparatus for failure of a fuel cell according to a second embodiment of the disclosure.

FIG. 8 is a schematic diagram of a prediction apparatus for failure of a fuel cell according to a second embodiment of the disclosure.

Referring to FIG. 8, the fuel cell 800 of the second embodiment includes a cell stack 804 composed of N single cells 802, a pair of current collectors 806a and 806b located at two sides of the cell stack 804, and a pair of end plates 808a and 808b respectively located next to the pair of current collectors 806a and 806b. Description of the single cells 802 in the cell stack 804 may refer to related description of the single cell 100 of the first embodiment, though the disclosure is not limited thereto. When the fuel cell 800 actually operates, each of the single cells 802 corresponds to one upstream voltage monitoring unit (for example, an upstream voltmeter 810) and one downstream voltage monitoring unit (for example, a downstream voltmeter 812), which are used to synchronously monitor voltage signals transmitted to a data processing unit 814 by each of the single cells 802. The data processing unit 814 includes a data acquisition unit 816 and a data operation unit 818. Voltage signals of each single cell 802 come from the upstream and down stream voltmeters 810 and 812 are transmitted to the data operation unit 818, and after obtaining the differential voltage ($DV_{cell}$) of each single cell 802, the signal is transmitted to the data acquisition unit 816. Meanwhile, a signal transmission unit 820 is used to transmit the voltage signals of each single cell into the data acquisition unit 816 to implement voltage monitoring of each of the single cells 802, and then transmits data to a system control unit 822 to perform correction control of failure prediction on the fuel cell 800.

Figure 9:
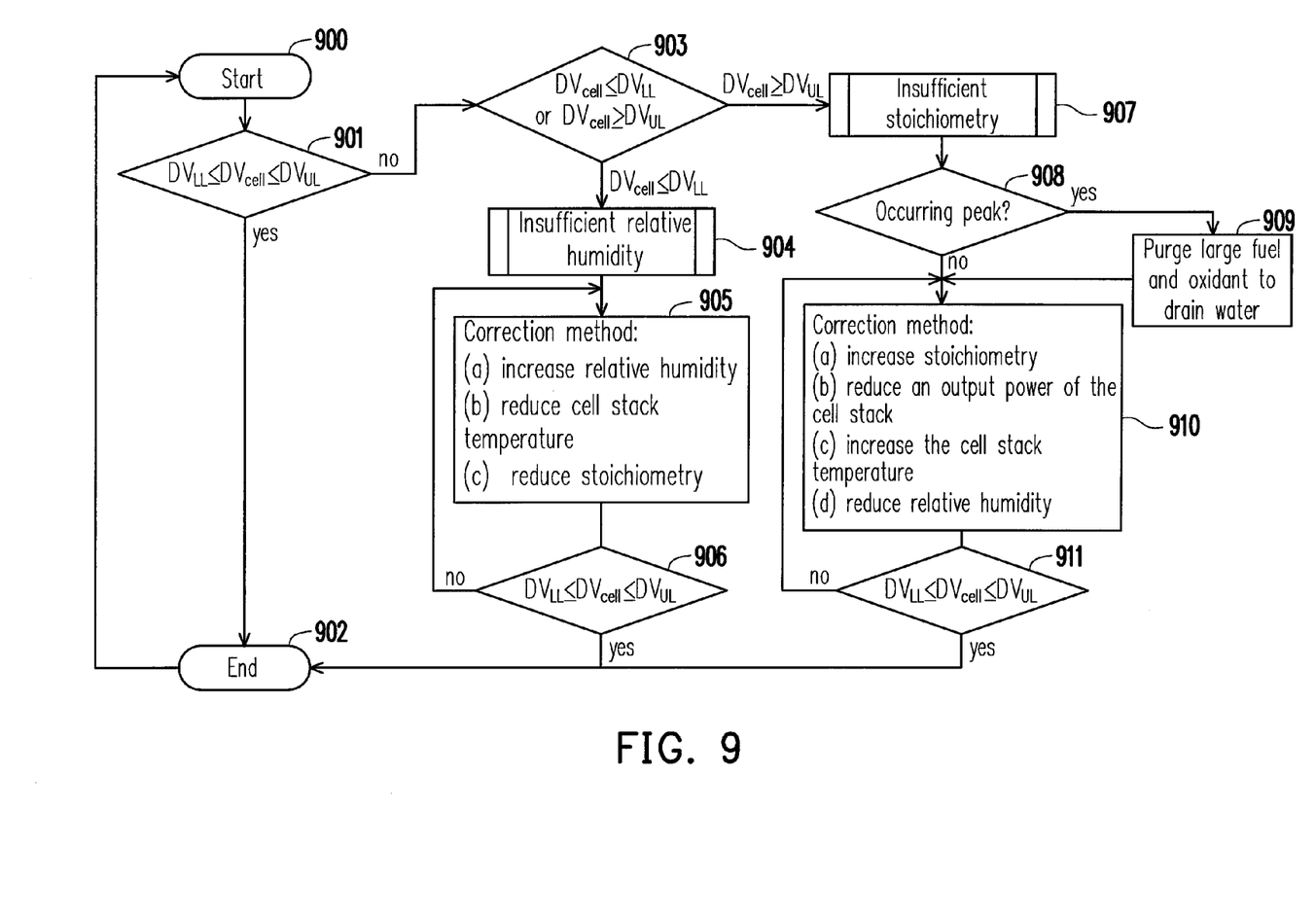
FIG. 9 is a flowchart illustrating a prediction method for failure of the fuel cell of FIG. 8.

FIG. 9 is a flowchart illustrating a prediction method for failure of the fuel cell of FIG. 8.

Referring to FIG. 9, after the system control unit 22 of FIG. 8 receives data of the differential voltage ($DV_{cell}$) of the upstream voltage and the downstream voltage of each of the single cells 802, determination of a cell state is started (900).

When the differential voltage is maintained within the tolerance interval ($DV_{LL} \leq DV_{cell} \leq DV_{UL}$) (901), it represents that the water control and stoichiometry control of the fuel cell is in a good state, and the determination is completed (902).

When the differential voltage is not in the tolerance interval, the state determination is performed ($DV_{cell} \leq DV_{LL}$ or $DV_{cell} \geq DV_{UL}$) (903).

When $DV_{cell} \leq DV_{LL}$, it represents that the cell water control is improper (the relative humidity is insufficient) (904), and a humidity correction method is performed (905), which includes: (A) increasing the relative humidity, or (B) reducing a temperature of the cell stack, or (C) reducing the stoichiometry, etc. When the differential voltage $DV_{cell}$ returns back to the tolerance interval ($DV_{LL} \leq DV_{cell} \leq DV_{UL}$) (906), the correction measure is ended (902).

When $DV_{cell} \geq DV_{UL}$, it represents that the cell stoichiometry control is improper (the stoichiometry is insufficient) (907), and it is first determined whether a peak occurs (908). When the peak occurs (an amplitude and a frequency thereof reach a predetermined condition), a large amount of fuel and oxidant are used to drain the liquid water till the occurrence of peak is stop. Then, a correction method of stoichiometry is performed (910), which includes: (A) increasing the stoichiometry, or (B) reducing an output power of the cell stack, or (C) increasing the temperature of the cell stack, or (D) reducing the relative humidity, etc. When the differential voltage $DV_{cell}$ returns back to the tolerance interval ($DV_{LL} \leq DV_{cell} \leq DV_{UL}$) (911), the correction measure is ended (902).

The aforementioned fuel cell failure prediction and precaution are cyclically performed.

In summary, in the disclosure, by monitoring a differential voltage between the upstream and the downstream of the electrochemical flow field and a developing trend thereof in each single cell, improper water control and stoichiometry control in the fuel cell are corrected, so as to predict and monitor the cell failure via a fast, accurate, sensitive, simple, cheap, on-line, real-time, in-situ and non-invasion detecting method.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A prediction apparatus for failure of a fuel cell, wherein the fuel cell comprises at least one single cell, the prediction apparatus comprising:

an upstream voltage monitoring unit, corresponding to each of the single cells and synchronously monitoring an upstream voltage of an anode flow field plate and a cathode flow field plate in each of the single cell;

a downstream voltage monitoring unit, corresponding to each of the single cells and synchronously monitoring a downstream voltage of a pair of current collectors;

a data processing unit, receiving voltage signals of the upstream voltage and the downstream voltage transmitted by the upstream voltage monitoring unit and the downstream voltage monitoring unit to obtain a differential voltage of the upstream voltage and the downstream voltage of each of the single cell; and a system control unit, configured to perform a correction of improper water control when the differential voltage is lower than a lower limit of a tolerance interval, and configured to perform a correction of improper stoichiometry control when the differential voltage is higher than an upper limit of the tolerance interval.

2. The prediction apparatus for failure of the fuel cell as claimed in claim 1, wherein the upstream voltage monitoring unit comprises an upstream voltmeter, and the downstream voltage monitoring unit comprises a downstream voltmeter.

3. The prediction apparatus for failure of the fuel cell as claimed in claim 1, wherein the single cell comprises:

a membrane electrode assembly;

the anode flow field plate, comprising an anode flow channel for transporting fuel;

the cathode flow field plate, comprising a cathode flow channel for transporting oxidant;

an anode gas diffusion layer, located between the membrane electrode assembly and the anode flow field plate; and a cathode gas diffusion layer, located between the membrane electrode assembly and the cathode flow field plate.

4. The prediction apparatus for failure of the fuel cell as claimed in claim 3, wherein the fuel cell further comprising:

a fuel inlet manifold, connected to an inlet of the anode flow channel of each single cell;

a fuel outlet manifold, connected to an outlet of the anode flow channel of each single cell;

an oxidant inlet manifold, connected to an inlet of the cathode flow channel of each single cell; and an oxidant outlet manifold, connected to an outlet of the cathode flow channel of each single cell.

5. The prediction apparatus for failure of the fuel cell as claimed in claim 1, wherein the data processing unit comprises a data acquisition unit and a data operation unit.

6. The prediction apparatus for failure of the fuel cell as claimed in claim 1, wherein the correction control of failure prediction is performed on the fuel cell according to the differential voltage and a tolerance interval.

7. The prediction apparatus for failure of the fuel cell as claimed in claim 1, wherein the correction of improper water control is at least one of measures of increasing relative humidity, reducing a temperature of the fuel cell and reducing stoichiometry.

8. The prediction apparatus for failure of the fuel cell as claimed in claim 1, wherein the correction of improper stoichiometry control is at least one of measures of increasing stoichiometry, reducing an output power of the fuel cell, increasing a temperature of the fuel cell and reducing relative humidity.

9. The prediction apparatus for failure of the fuel cell as claimed in claim 6, wherein the correction control of failure prediction further comprises a correction of liquid water overflow when the differential voltage is higher than the upper limit of the tolerance interval and a momentary peak occurs.

10. The prediction apparatus for failure of the fuel cell as claimed in claim 9, wherein the correction of liquid water overflow comprises supplying fuel and oxidant to the single cell to drain liquid water.

11. A prediction method for failure of a fuel cell, wherein the fuel cell comprises at least one single cell, the prediction method comprising:
   measuring an upstream voltage of an anode flow field plate and a cathode flow field plate in each of the single cell and a downstream voltage of a pair of current collectors to obtain a differential voltage of the upstream voltage and the downstream voltage; and
   determining whether the differential voltage is within a tolerance interval, and performing a correction of improper water control when the differential voltage is lower than a lower limit of the tolerance interval, and performing a correction of improper stoichiometry control when the differential voltage is higher than an upper limit of the tolerance interval.

12. The prediction method for failure of the fuel cell as claimed in claim 11, wherein the step of measuring the upstream voltage and the downstream voltage comprises using an upstream voltmeter and a downstream voltmeter to respectively measure the upstream voltage and the downstream voltage.

13. The prediction method for failure of the fuel cell as claimed in claim 11, wherein the correction of improper water control is at least one of measures of increasing relative humidity, reducing a temperature of the fuel cell and reducing stoichiometry.

14. The prediction method for failure of the fuel cell as claimed in claim 11, wherein the correction of improper stoichiometry control is at least one of measures of increasing stoichiometry, reducing an output power of the fuel cell, increasing a temperature of the fuel cell and reducing relative humidity.

15. The prediction method for failure of the fuel cell as claimed in claim 11, further comprising performing a correction of liquid water overflow when the differential voltage is higher than the upper limit of the tolerance interval and a momentary peak occurs.

16. The prediction method for failure of the fuel cell as claimed in claim 15, wherein the correction of liquid water overflow comprises supplying fuel and oxidant to the single cell to drain liquid water.

* * * * *